United States Patent [19]

Iwahara et al.

[11] Patent Number: 4,722,807
[45] Date of Patent: Feb. 2, 1988

[54] STABILIZER FOR ACRYLOYLOXYSILANE COMPOUNDS

[75] Inventors: Takahisa Iwahara; Tetsu Katsutani, both of Kobe, Japan

[73] Assignee: Kanegafuchi Kagaku Kogyo Kabushiki Kaisha, Osaka, Japan

[21] Appl. No.: 622,908

[22] Filed: Jun. 21, 1984

[30] Foreign Application Priority Data

Jun. 21, 1983 [JP] Japan ................................ 58-111295

[51] Int. Cl.$^4$ ......................... C09K 15/08; C07F 7/02
[52] U.S. Cl. ..................................... 252/404; 556/401
[58] Field of Search ......................... 252/404; 556/401

[56] References Cited

U.S. PATENT DOCUMENTS

| | | | |
|---|---|---|---|
| 3,258,477 | 6/1966 | Plueddemann et al. | 556/440 |
| 3,554,962 | 1/1971 | Fischer | 524/91 |
| 4,563,538 | 1/1986 | Wakabayashi et al. | 556/401 |

FOREIGN PATENT DOCUMENTS

| | | |
|---|---|---|
| 1183503 | 12/1964 | Fed. Rep. of Germany ...... 556/401 |
| 1360469 | 3/1964 | France . |
| 1339017 | 11/1973 | United Kingdom . |

OTHER PUBLICATIONS

*Encyclopedia of Polymer Science and Technology,* vol. 7, p. 648.
Chem. Abstr. vol. 54(6) (1960), 5538(g)–5539(b), "Reactions of Free Radicals . . . ".
Chem. Abstr. vol. 52(9) (1958), 7218(i)–7219(e), "Reactions of Free Radicals . . . ".
Hawley, Gessner G. (Ed.), *The Condensed Chemical Dictionary,* Van Nostrand Reinhold Co. 1977, p. 274.
Chem. Abstr. 97:39875s, "Polyurethane Compositions", vol. 97, 1982, pp. 35–36.
Chem. Abstr. 96:162257y, "Polymer-Supported Periodate and Iodate as Oxidizing Agents", vol. 96, 1982, p. 712.
Chem. Abstr. 88:152256t, "Bis-(2-hydroxyethyleneterephthalate)", vol. 88, 1978, p. 573.

*Primary Examiner*—Matthew A. Thexton
*Attorney, Agent, or Firm*—Armstrong, Nikaido, Marmelstein & Kubovcik

[57] ABSTRACT

A stabilizer useful for inhibiting polymerization of γ-acryloyloxypropyltrimethoxysilane and γ-methacryloyloxypropyltrimethoxysilane comprising 2,5-di-t-butylhydroquinone and an alcohol.

2 Claims, No Drawings

STABILIZER FOR ACRYLOYLOXYSILANE COMPOUNDS

BACKGROUND OF THE INVENTION

The present invention relates to a stabilizer applied to acryloyloxysilane compounds, and more particularly to a stabilizer useful for inhibiting polymerization of specific acryloyloxysilane compounds.

Esters of acrylic acid and methacrylic acid have a tendency to easily polymerize. The polymerization reaction occurs by mere heating, and they produce polymers having a relatively high molecular weight. It has been recognized that the stability of an acrylate and methacrylate having a hydrolyzable silicon group, such as trimethoxysilyl group, linking to ester group through an alkylene group, represented by the general formula:

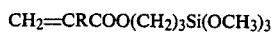

$$CH_2=CRCOO(CH_2)_3Si(OCH_3)_3$$

wherein R is hydrogen atom or methyl group, is worst among various known acrylates and methacrylates. In the production of these acryloyloxysilane and methacryloyloxysilane compounds (hereinafter referred to as "acryloyloxysilane compounds"), particularly in a purification step of a crude product containing predominantly the acryloyloxysilane compounds, they cause troubles owing to their unstability. Even if polymerization inhibitors usually applied to acrylates and methacrylates, e.g., hydroquinone and 2,5-di-t-butylhydroquinone, are added to the crude product, the problem cannot be solved and they change into a gel in the purification step, thus losing commercial value.

It is an object of the present invention to provide a stabilizer for the acryloyloxysilane compounds.

A further object of the present invention is to provide a stabilizer useful for stabilization of the acryloyloxysilane compounds under heating and reduced pressure, particularly useful for inhibiting polymerization of the acryloyloxysilane compounds in the purification of the crude product thereof.

These and other objects of the present invention will become apparent from the description hereinafter.

SUMMARY OF THE INVENTION

In accordance with the present invention, there is provided a stabilizing composition for γ-acryloyloxypropyltrimethoxysilane and γ-methacryloyloxypropyltrimethoxysilane comprising 2,5-di-t-butylhydroquinone and an alcohol.

DETAILED DESCRIPTION

The stabilizer of the present invention is useful for stabilization of silane compounds represented by the general formula (1):

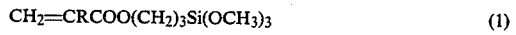

$$CH_2=CRCOO(CH_2)_3Si(OCH_3)_3 \quad (1)$$

where R is hydrogen atom or methyl group. The stabilizer is used in an amount effective for stabilizing the silane compounds (1). It is well known that 2,5-di-t-butylhydroquinone is useful as an inhibitor for usual acrylic monomers, but it has not been known that the composition comprising a combination of 2,5-di-t-butylhydroquinone and an alcohol has a remarkable effect on stabilization of the above silane compounds (1). The combination use produces a synergistic stabilizing effect which cannot be obtained by the single use of each compound. This has an industrially important meaning in that it is possible to prevent change in quality owing to heating conducted in usual purification and distillation operations of the crude product containing the silane compound and change in quality on storage for a long term.

Representative examples of the alcohol used in the present invention are, for instance, an aliphatic monohydric alcohol such as methanol, ethanol, propanol, isopropanol or t-butanol, an aliphatic polyhydric alcohol such as ethylene glycol, diethylene glycol or glycerol, a monoalkyl ether of the aliphatic polyhydric alcohol such as ethylene glycol monomethyl ether, diethylene glycol monomethyl ether or glycerol monomethyl ether, and the like. Methanol is particularly preferred.

2,5-Di-t-butylhydroquinone and the alcohol can be used in arbitrary ratios. Preferably, the ratio of 2,5-di-t-butylhydroquinone to the alcohol is from 1:0.1 to 1:100 by weight. They can be used in a manner such as separately adding each component to the silane compound, or previously admixing both components and adding the mixture to the silane compound. Preferably, 2,5-di-t-butylhydroquinone and the alcohol are used in the form of a mixture thereof.

In general, 2,5-di-t-butylhydroquinone is used in an amount of 0.05 to 1% by weight based on the silane compound, but the amount is not particularly limited so long as the polymerization of the silane compound can be inhibited.

The present invention is more specifically described and explained by means of the following Examples, in which all % are by weight unless otherwise noted. It is to be understood that the present invention is not limited to the Examples, and various changes and modifications may be made in the invention without departing from the spirit and scope thereof.

EXAMPLE 1

To a 20 ml. test tube were added 2 g. of a crude product containing predominantly γ-methacryloyloxypropylmethoxysilane obtained by reaction of γ-methacryloyloxypropyltrichlorosilane and methanol (γ-methacryloyloxypropyltrimethoxysilane content in the crude product measured by gas chromatography: 88 %), 20 mg of 2,5-di-t-butylhydroquinone and 20 mg. of methanol. A condenser was attached to the test tube, and the test tube was dipped in an oil bath maintained at 150° C. with air cooling. The mixture in the test tube did not lose its flowability even after 3 hours.

The above procedure was repeated except that only 2,5-di-t-butylhydroquinone was added to the crude product in an amount of 1%. After 80 minutes, the mixture in the test tube lost its flowability and changed into a gel. In case of the crude product itself to which no stabilizer was added, it gelled after 15 minutes.

EXAMPLE 2

To a 20 ml. test tube were added 4 g. of a crude product containing 93% of γ-methacryloyloxypropylmethoxysilane prepared by the same method as in Example 1, 40 mg. of 2,5-di-t-butylhydroquinone and 40 mg. of methanol. A condenser equipped with a three-way stopcock was attached to the test tube. After degassing at 3 mmHg for 20 minutes, the test tube was dipped under 3 mmHg in an oil bath maintained at 150° C., while making water flow through the condenser and shaking occasionally the tube. The mixture in the tube did not lose its flowability even after 1 hour, and no gel formation was observed. The mixture subjected to the gelling test contained 90% of γ-methacryloyloxypropyltrimethoxysilane.

The above procedure was repeated except that only 2,5-di-t-butylhydroquinone was added to the crude product in an amount of 1%. After 1 hour, the mixture in the test tube increased its viscosity, and 5% of the mixture gelled.

Further, the above procedure was repeated except that no stabilizer was added to the crude product. After 1 hour, the crude product increased its viscosity, and 10% of the crude product gelled.

EXAMPLE 3

To 100 g. of the crude product used in Example 2 containing 93% of γ-methacryloyloxypropylmethoxysilane were added 0.5 g. of 2,5-di-t-butylhydroquinone and 0.5 g. of methanol, and the mixture was subjected to purification by using a usual distillation apparatus. There was recovered 85 g. of pure γ-methacryloyloxypropyltrimethoxysilane. The yield was 85%.

The above procedure was repeated except that no stabilizer was added to the crude product, but it promptly gelled and the distillation was impossible.

In addition to the ingredients used in the Examples, other ingredients can be used in the Examples as set forth in the specification to obtain substantially the same results.

What we claim is:

1. A composition which comprises one of γ-acryloyloxypropyltrimethoxysilane and γ-methacryloyloxypropyltrimethoxysilane, and a stabilizing effective amount of 2,5-di-tert-butylhydroquinone and an alcohol which are present in a ratio of 1:0.1 to 1:100 by weight.

2. The composition of claim 1, wherein the alcohol is methyl alcohol.

* * * * *